(12) United States Patent
Cong et al.

(10) Patent No.: US 9,240,039 B2
(45) Date of Patent: Jan. 19, 2016

(54) METHOD FOR FAST TEST STRIP INTENSITY RECOGNITION

(71) Applicants: Ge Cong, Pleasanton, CA (US); Lijun Wu, Pleasanton, CA (US); Richard Cong, Pleasanton, CA (US)

(72) Inventors: Ge Cong, Pleasanton, CA (US); Lijun Wu, Pleasanton, CA (US); Richard Cong, Pleasanton, CA (US)

( * ) Notice: Subject to any disclaimer, the term of this patent is extended or adjusted under 35 U.S.C. 154(b) by 0 days.

(21) Appl. No.: 14/169,066

(22) Filed: Jan. 30, 2014

(65) Prior Publication Data
US 2014/0219885 A1   Aug. 7, 2014

Related U.S. Application Data

(60) Provisional application No. 61/759,899, filed on Feb. 1, 2013.

(51) Int. Cl.
| | |
|---|---|
| *G01N 33/00* | (2006.01) |
| *G06T 7/00* | (2006.01) |
| *G01N 33/558* | (2006.01) |
| *G01N 21/84* | (2006.01) |
| *G01N 33/543* | (2006.01) |
| *G01N 21/17* | (2006.01) |

(52) U.S. Cl.
CPC .............. *G06T 7/00* (2013.01); *G01N 21/8483* (2013.01); *G01N 33/54393* (2013.01); *G01N 33/558* (2013.01); *G01N 2021/1748* (2013.01)

(58) Field of Classification Search
CPC ................................ G06T 7/00; G01N 33/558
See application file for complete search history.

(56) References Cited

U.S. PATENT DOCUMENTS

| | | | | |
|---|---|---|---|---|
| 7,652,268 B2 * | 1/2010 | Patel | ........................... | 250/484.5 |
| 2011/0293153 A1 * | 12/2011 | Plickert et al. | ................ | 382/128 |

* cited by examiner

*Primary Examiner* — Sam P Siefke
(74) *Attorney, Agent, or Firm* — Perkins Coie LLP; Viola T. Kung

(57) ABSTRACT

Techniques for fast and accurate measuring test strip intensities are disclosed herein. A method for measuring a test strip intensity comprising steps of obtaining an image of a sample line in a test strip and a plurality of reference lines, wherein the reference lines have known intensities; determining grayscale values of the sample line and the reference lines from the image; constructing a standard curve based on the grayscale values versus the known intensities of the reference lines; and determining the intensity of the sample line by fitting the grayscale value of the sample line on the standard curve.

15 Claims, 16 Drawing Sheets

METHOD FOR FAST TEST STRIP INTENSITY RECOGNITION

CROSS-REFERENCE TO RELATED APPLICATION

This application claims the benefit of U.S. Provisional Patent Application No. 61/759,899, entitled "SYSTEMS AND METHODS FOR FAST TEST STRIP INTENSITY RECOGNITION", filed on Feb. 1, 2013, which is incorporated by reference herein in its entirety.

FIELD OF THE INVENTION

This invention relates generally to medical test strip systems, and in particular to a system for fast and accurate test strip intensity recognition.

BACKGROUND

Test strips are basic diagnostic instruments that are commonly used in various applications such as pregnancy test, drug test, and diabetes test. The test strip technology is widely used in different areas including medicine, biology, and food safety.

However, test strip technology is considered inaccurate for many reasons. Different manufacture batches of the test strips can have variations on colors and intensities. To receive quantitative result, a human operator has to compare the test strip with a reference card. This introduces subjective human errors. There are dedicated machines for accurately reading the test strip results. But these machines are typically expensive and cumbersome to move, and requires professional training on how to operate the machines.

DETAILED DESCRIPTION

Figure 1:
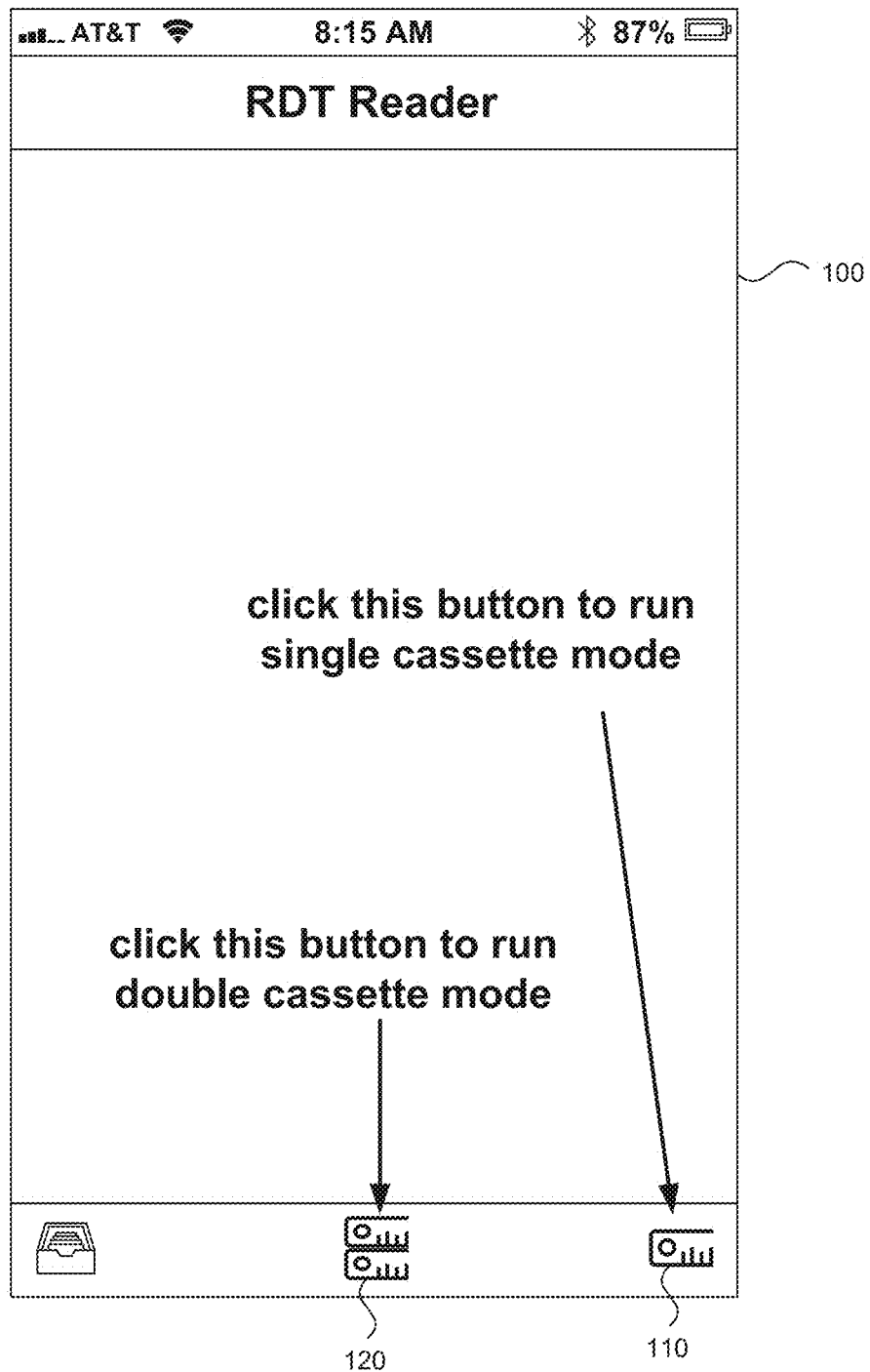
FIG. 1 illustrates a screenshot showing main interface 100 of an example computer application for fast test strip intensity recognition.
Figure 2A:
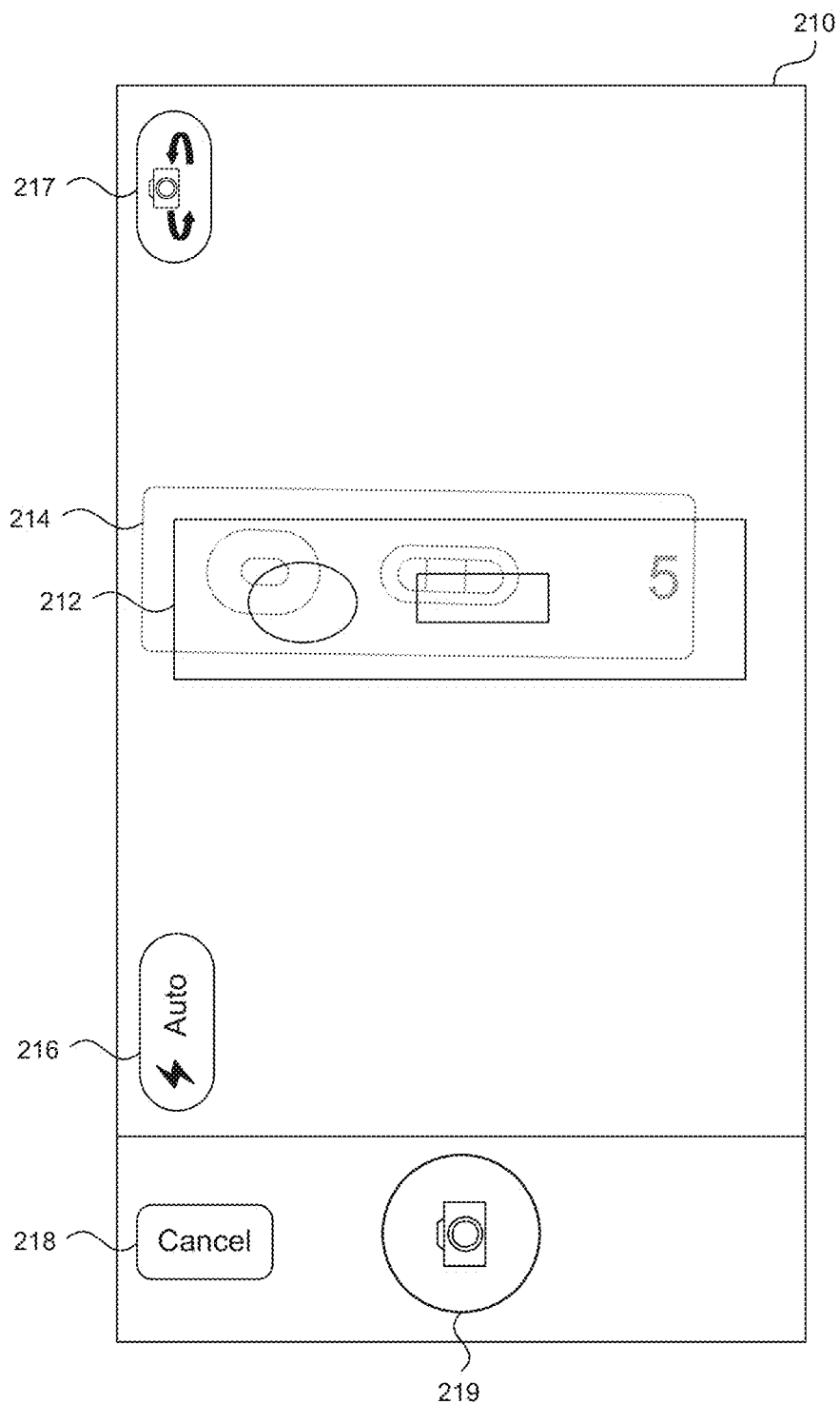
FIG. 2A illustrates a screenshot showing a single cassette mode capture interface of an example computer application.
Figure 2B:
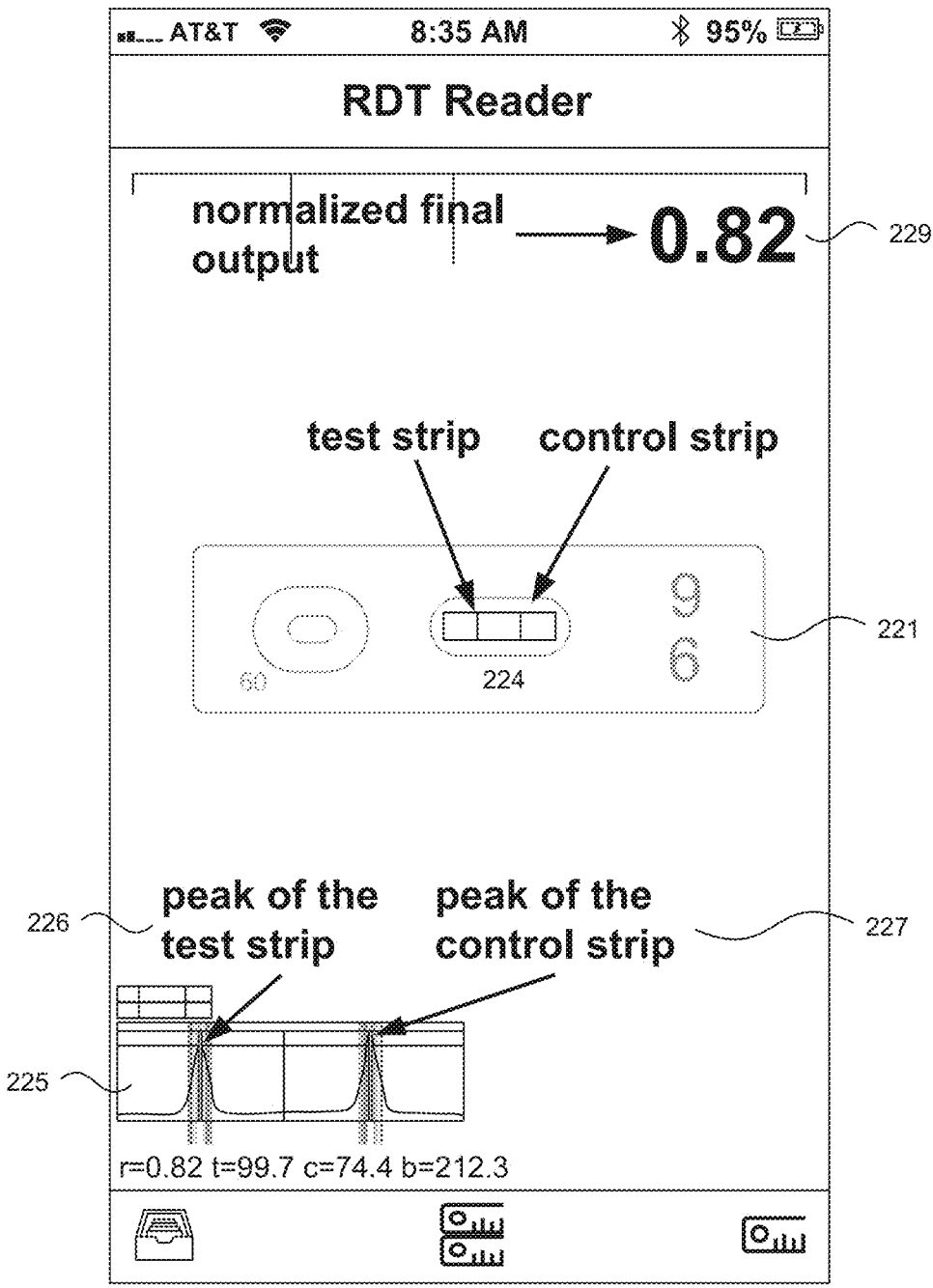
FIG. 2B illustrates a screenshot showing a single cassette mode result interface of an example computer application.
Figure 4A:
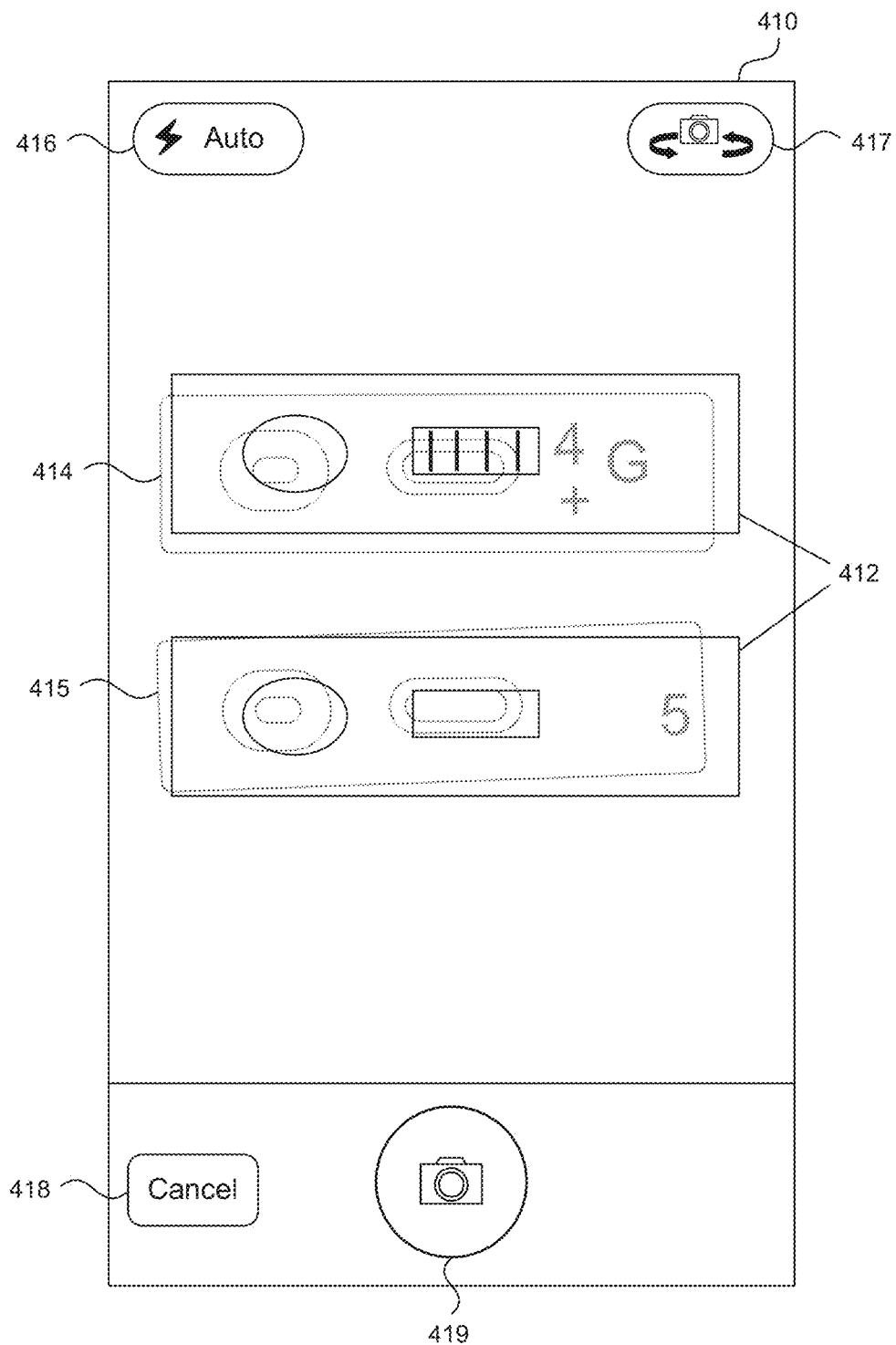
FIG. 4A illustrates a screenshot showing a double cassette mode capture interface of an example computer application.
Figure 4B:
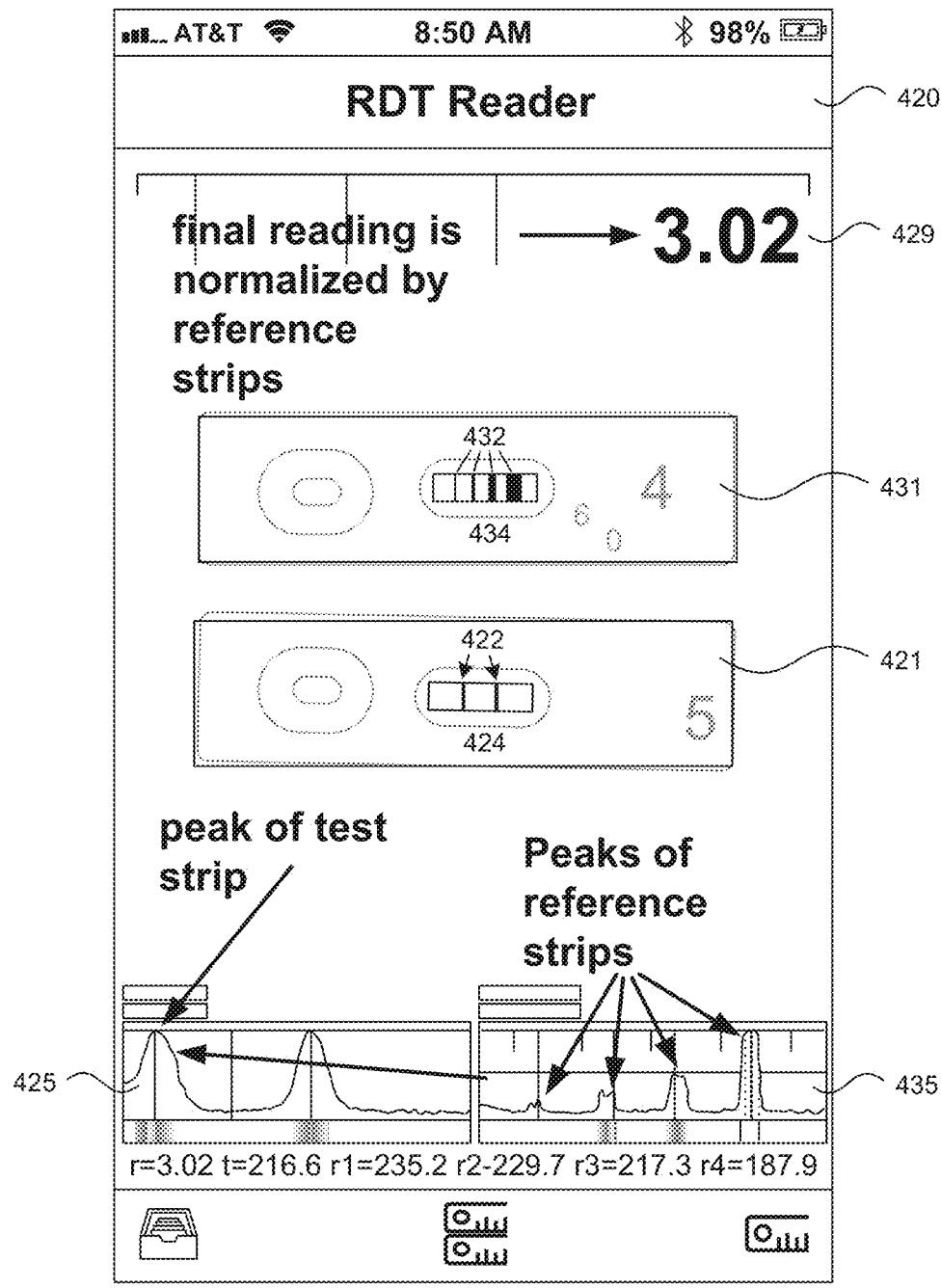
FIG. 4B illustrates a screenshot showing a double cassette mode analysis interface of an example computer application.

FIG. 1 illustrates a screenshot showing a main interface 100 of an example computer application for fast test strip intensity recognition. After the computer application launches, the computer application shows the main interface 100. The main interface 100 provides two buttons 110 and 120 for a user to choice between a single cassette mode and a double cassette mode. If the user chooses the single cassette mode by clicking the button 110, the computer application switches to a single cassette mode interface as illustrated in FIGS. 2A and 2B. If the user chooses the double cassette mode by clicking the button 120, the computer application switches to a double cassette mode interface as illustrated in FIGS. 4A and 4B.

The computer application is designed to run on at least one computer device. The computer device can be a desktop computer, a laptop, a tablet computer, a smart phone, a personal digital assistant (PDA), a digital camera, or other type of electronic device capable of running the computer application. For instance, the computer application can be designed to run on an Apple iPhone smart phone, or an Android smart phone.

FIG. 2A illustrates a screenshot showing a single cassette mode capture interface 210 of an example computer application. After the user clicks the button 110 as shown in the FIG. 1, the computer application shows the single cassette mode capture interface 210 for capturing a picture of a test strip cassette.

The user places a treated cassette on a surface, preferably a dark surface. The cassette has been treated with test fluid, such as urine or blood sample. The user aims the camera of the computer device running the computer program to the cassette. The image of the cassette is visualized in the single cassette mode capture interface 210, as shown in the FIG. 2A.

In one embodiment, the single cassette mode capture interface 210 includes an overlay frame 212 visualized on the interface 210. The overlay frame 212 mimics the overall shape of the cassette to prompt the user to adjust the computer device to a proper position and angle so that the image of the cassette 214 closely fit the overlay frame 212, in order to achieve consistent capturing of the image of the cassette. For instance, the overlay frame 212 illustrated in the FIG. 2A has an outer rectangle mimicking the outer rectangular shape of the cassette. Additionally, the overly frame 212 has an oval and an inner rectangle mimicking the test drop window and the test strip window of the cassette. The oval and the inner rectangle prompt the user to lay down the cassette for image capturing in a proper orientation, as suggested by the positions of the oval and the inner rectangle. An exact match between the rectangle and the cassette's border, however, is not required for capturing the image of the cassette.

Optionally, the single cassette mode capture interface 210 can include a flash option button 216 to switch between flash modes. For instance, in one embodiment, the flash modes include Auto, On and Off modes. The device capturing the image can be equipped with flash component to improve the image quality. In one embodiment, the single cassette mode capture interface 210 can further include a load button. After the user clicks the load button, the computer program loads and processes a saved image, instead of capturing a new image for processing. The single cassette mode capture interface 210 can also include a cancel button 218. If the user clicks the cancel button 218, the computer program switches back to the main interface 100 as shown in the FIG. 1.

Figure 3:
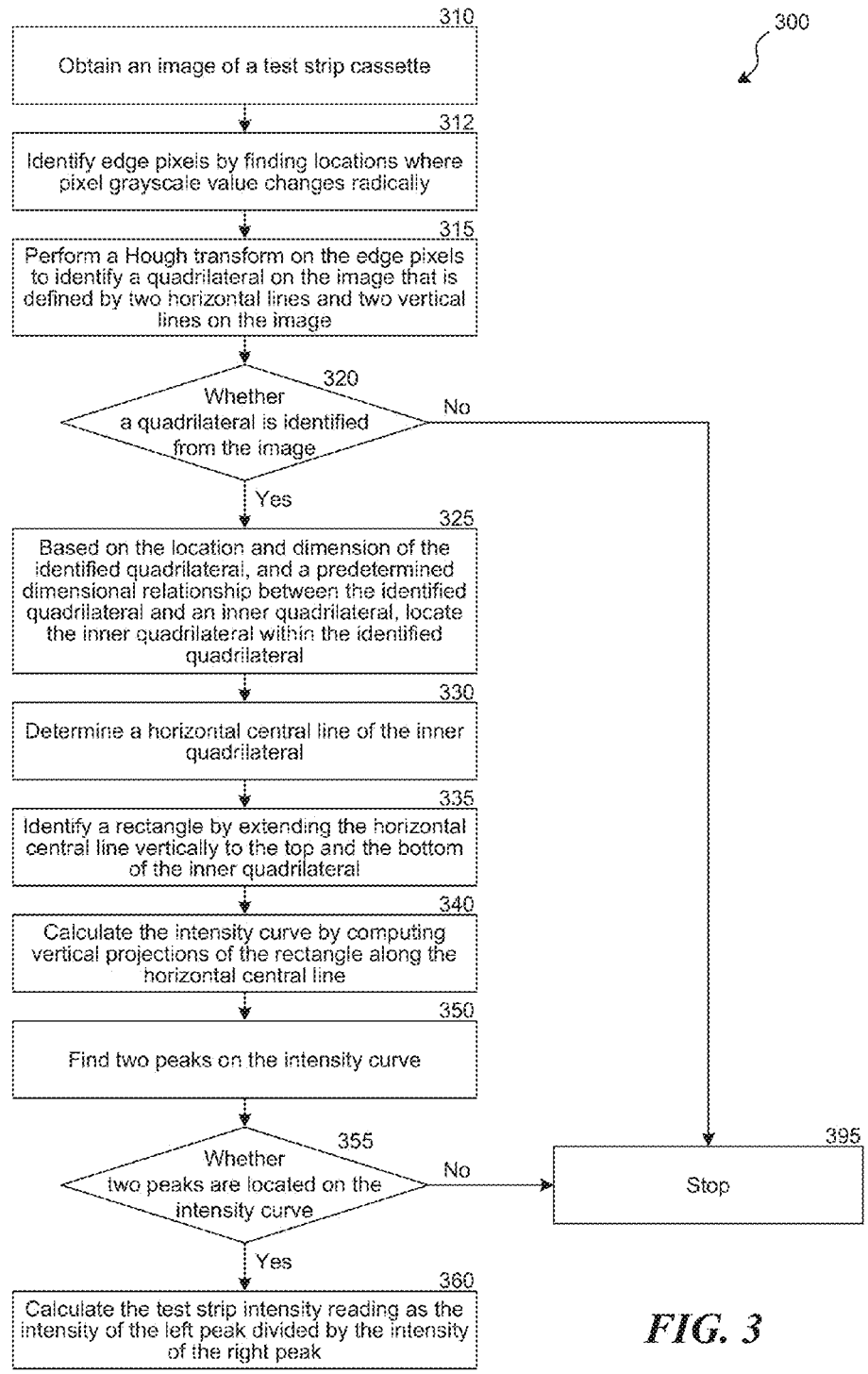
FIG. 3 illustrates an example process of analyzing a test strip image.

The user can click a capture button 219 to capture the image of the cassette. Then the computer program analyzes the captured image of the cassette and switches to a single cassette mode result interface 220 as illustrated in FIG. 2B. To analyze the captured image, the computer program can follow the process 300 as illustrated in FIG. 3.

In one embodiment, the cassette includes a test drop window and a test strip window. The cassette is treated with test fluid, such as urine or blood sample, by dropping the test fluid onto the test drop window. Once the cassette is treated, two strips will be visualized in the test strip window. One of the strips is a test strip, whose intensity indicates the test result. The other strip is a control strip providing a standardized reference for the intensity reading. The image of the cassette captured by the computer program includes the images of test strip and the control strip.

FIG. 2B illustrates a screenshot showing a single cassette mode result interface 220 of an example computer application. The result interface 220 visualizes a captured image 221 of the cassette, which includes test strip image 222 and control strip image 223.

The single cassette mode result interface 220 further visualizes an intensity curve 225 showing the intensity of the test strip window 224 along an axis of the test strip window 224 that is perpendicular to the test strip line. The intensity curve 225 can be calculated by the computer program using the captured image via a process illustrated in FIG. 3. The intensity curve 225 has two peaks 226 and 227. Peak 226 corresponds to the intensity of test strip 222, peak 227 corresponds to the intensity of the control strip 223. The result interface 220 further displays a test strip intensity reading 229. The test strip intensity reading 229 is calculated by the computer program via the process illustrated in FIG. 3.

FIG. 3 illustrates an example process 300 of analyzing a test strip image. At step 310, the computer program obtains an image of a test strip cassette. In one embodiment, the computer program obtains the image by capturing an image of test strip cassette by using a camera of a computer device on which the computer program runs. At step 312, the computer program identifies edge pixels by find locations (i.e. pixels) where pixel grayscale value changes radically. At step 315, the computer program performs a Hough transform on edge pixels to identify a quadrilateral on the image that is defined by two horizontal lines and two vertical lines on the image. Hough transform is a feature extraction technique used in image analysis. Hough transform technique can find instances of lines within a certain class of shapes by a voting procedure. In one embodiment, other feature extraction technique, other than the Hough transform, can be used to identify the quadrilateral, as readily understood by a person having ordinary skill in the art.

At step 320, the computer program checks whether a quadrilateral is identified from the image. If a quadrilateral is identified, the computer program continues to step 325. The identified quadrilateral indicates the shape and location of the cassette on the image. Otherwise, the computer program stops at step 395.

At step 325, based on the location and dimension of the identified quadrilateral, and a predetermined dimensional relationship between the identified quadrilateral and an inner quadrilateral, the computer program locates the inner quadrilateral within the identified quadrilateral. The inner quadrilateral indicates the shape and location of the test strip window on the image.

At step 330, the computer program determines a horizontal central line of the inner quadrilateral. The horizontal central line can be roughly horizontal along the inner quadrilateral. However, the horizontal central line is not required to be at zero degree from any axis of the inner quadrilateral. The horizontal central line is the X-axis of an intensity curve to be calculated by the computer program. At step 335, the computer program identifies a rectangle by extending the horizontal central line to a pre-defined distance vertically towards the top and the bottom of the inner quadrilateral. In case when the image of the test strip window happens to be rectangular, the identified rectangle closely fit the image of the test strip window.

At step 340, the computer program calculates the intensity curve by computing vertical projection of the rectangle along the horizontal central line. In one embodiment, the computer program reads pixels of the image portion within the rectangle, and aggregates the pixel values along the direction that is perpendicular to the central line as the intensity curve values along the horizontal central line (X-Axis).

At step 350, the computer program finds two peaks on the intensity curve. In the embodiment as illustrated in FIG. 2B, the left peak corresponds to the intensity of the test strip, and the right peak corresponds to the intensity of the control strip.

At step 355, the computer program checks whether two peaks are located on the intensity curve. If two peaks are located, the computer program continues to step 360. Otherwise, the computer program stops at step 395.

At step 360, the computer program calculates the test strip intensity reading as the intensity of the test peak divided by the intensity of the control peak.

Similarly to the single cassette mode, the computer program can provide a double cassette mode for accurate recognition of the test strip intensity reading. If a user clicks the button 120 as illustrated in the FIG. 1, the computer program switches to a double cassette mode interface as illustrated in FIGS. 4A and 4B.

FIG. 4A illustrates a screenshot showing a double cassette mode capture interface 410 of an example computer application. The user places a treated test cassette and a reference cassette on a surface, preferably a dark surface. The test cassette has been treated with test fluid, such as urine or blood sample. The user aims the camera of the computer device running the computer program to the cassettes. In the embodiment illustrated in the FIG. 4A, the reference cassette is placed on top of the test cassette. In some other embodiment, the computer program can automatically recognize the reference cassette and the test cassette; therefore the positions of the cassette do not matter. The image of the cassettes is visualized in the double cassette mode capture interface 410, as shown in the FIG. 4A.

In one embodiment, the double cassette mode capture interface 410 includes an overlay frame 412 visualized on the interface 410. The overlay frame 412 mimics the overall shapes of the test cassette and the reference cassette to prompt the user to adjust the computer device and the cassettes to proper positions and angles so that the images of the cassettes 414 and 415 closely fit the overlay frame 412, in order to achieve consistent capturing of the image of the cassettes. For instance, the overlay frame 412 illustrated in the FIG. 4A has an upper rectangle mimicking the outer rectangular shape of the reference cassette, and a lower rectangle mimicking the outer rectangular shape of the test cassette. Additionally, the overly frame 412 has ovals and inner rectangles mimicking the test drop windows and the inner strip windows of the cassettes. The ovals and the inner rectangles prompt the user to lay down the test cassette and the reference cassette for image capturing in a proper orientation, as suggested by the positions of the oval and the inner rectangle. In one embodiment, the top portion of the overlay frame 412 has 4 bars in an inner strip window, which reminds the user to put the reference cassette on the top. In other embodiments, the overlay frame can contain numbers of bars other than 4, or to remind the user to put the reference cassette in other positions relative to the test cassette, as ready understood by a person having ordinary skill in the art. An exact match between the rectangles and the cassettes' borders, however, is not required for capturing the image of the cassettes.

Optionally, the double cassette mode capture interface 410 can include a flash option button 416 to switch between flash modes. For instance, in one embodiment, the flash modes include Auto, On and Off modes. The device capturing the image can be equipped with flash component to improve the image quality. In one embodiment, the double cassette mode capture interface 410 can further include a load button. After the user clicks the load button, the computer program loads and processes a saved image, instead of capturing a new image for processing. The double cassette mode capture interface 410 can also include a cancel button 418. If the user clicks the cancel button 418, the computer program switches back to the main interface 100 as shown in the FIG. 1.

Figure 5:
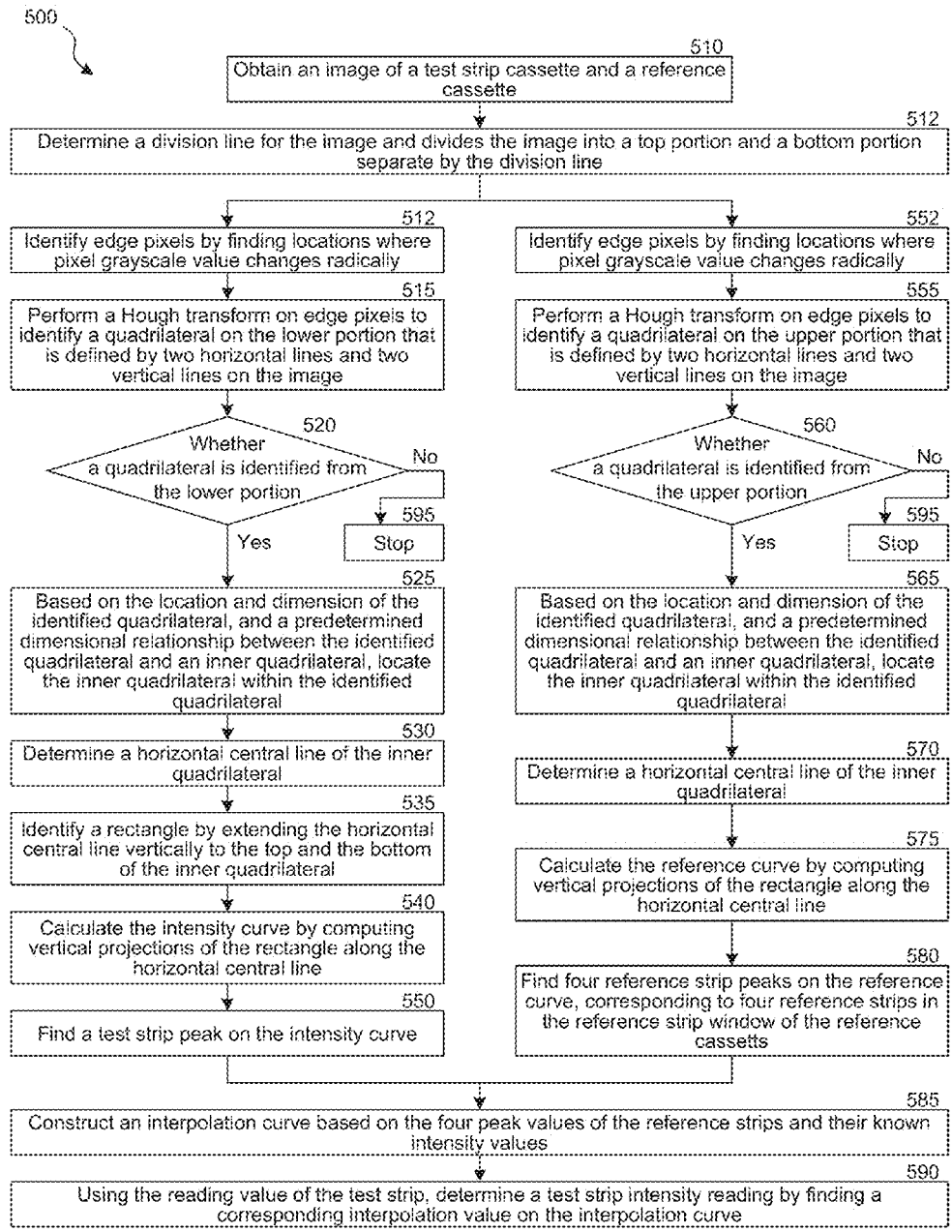
FIG. 5 illustrates an example process of analyzing a test strip image with reference strips.

The user can click a capture button 419 to capture the image of the cassette. Then the computer program analyzes the captured image of the cassette and switches to a double cassette mode result interface 420 as illustrated in FIG. 4B. To analyze the captured image, the computer program can follow the process 500 as illustrated in FIG. 5.

In one embodiment, the test cassette includes a test drop window and a test strip window. The test cassette is treated with test fluid, such as urine or blood sample, by dropping the test fluid onto the test drop window. Once the cassette is treated, a test strip will be visualized in the test strip window, whose intensity indicates the test result. In some embodiments, the test strip window includes another control strip providing a standardized reference for the intensity reading. The image of the cassette captured by the computer program includes the images of test strip and the control strip. The reference cassette includes a reference strip window. In one embodiment as illustrated in the FIG. 5, the reference strip window includes four reference lines (also referred to as reference strips). In another embodiment, the reference strip window can include from two to eight lines. In yet another embodiment, the reference strip window can includes a plurality of reference lines. The intensities of the reference lines are known. The computer program is able to determine the intensity of the test strip by comparing the image of the test strip with the images of the reference strips. In some embodiments, the reference lines are printed using computer generated images of lines having grayscale values that are predetermined by a user.

FIG. 4B illustrates a screenshot showing a double cassette mode result interface 420 of an example computer application. The result interface 420 visualizes a captured image 421 of the test cassette, which includes test strip image 422, and a captured image 431 of the reference cassette, which includes reference strips image 432.

The double cassette mode result interface 420 further visualizes an intensity curve 425 showing the intensity of the test strip window 424 along an axis of the test strip window 424 that is perpendicular to the test strip line. The intensity curve 425 can be calculated by the computer program using the captured image via a process illustrated in FIG. 5. The intensity curve 425 has a peaks 426 corresponding to the intensity of test strip 422.

The double cassette mode result interface 420 further visualizes a reference curve 435 showing the intensities of the reference strip window 434 along an axis of the reference strip window 434 that is perpendicular to the reference strip lines. The reference curve 435 can be calculated by the computer program using the captured image via a process illustrated in FIG. 5. The reference curve 435 has four peaks 436 corresponding to the intensities of the reference strips 432.

The result interface 420 further display a test strip intensity reading 429. The test strip intensity reading 429 is calculated by the computer program via the process illustrated in FIG. 5.

FIG. 5 illustrates an example process 500 of analyzing a test strip image with reference strips (also referred to as reference lines). At step 510, the computer program obtains an image of a test strip cassette and a reference cassette. In one embodiment, the computer program obtains the image by capturing an image of test strip cassette and a reference cassette by using a camera of a computer device on which the computer program runs. At step 512, the computer program determines a division line for the image and divides the image into a top portion and a bottom portion separate by the division line.

At step 512, the computer program identifies edge pixels by find locations (i.e. pixels) where pixel grayscale value changes radically. At step 515, the computer program performs a Hough transform on edge pixels to identify a quadrilateral on the lower portion that is defined by two horizontal lines and two vertical lines on the image. In one embodiment, other feature extraction technique, other than the Hough transform, can be used to identify the quadrilateral, as readily understood by a person having ordinary skill in the art.

At step 520, the computer program checks whether a quadrilateral is identified from the lower portion. If a quadrilateral is identified, the computer program continues to step 525. The identified quadrilateral indicates the shape and location of the test cassette on the image. Otherwise, the computer program stops at step 595.

At step 525, based on the location and dimension of the identified quadrilateral, and a predetermined dimensional relationship between the identified quadrilateral and an inner quadrilateral, the computer program locates the inner quadrilateral within the identified quadrilateral. The inner quadrilateral indicates the shape and location of the test strip window of the test cassette on the lower portion of the image.

At step 530, the computer program determines a horizontal central line of the inner quadrilateral. The horizontal central line can be roughly horizontal along the inner quadrilateral. However, the horizontal central line is not required to be at zero degree from any axis of the inner quadrilateral. The horizontal central line is the X-axis of an intensity curve to be calculated by the computer program. At step 535, the computer program identifies a rectangle by extending the horizontal central line vertically to a pre-defined distance towards the top and the bottom of the inner quadrilateral. In case when the image of the test strip window happens to be rectangular, the identified rectangle closely fit the image of the test strip window.

At step 540, the computer program calculates the intensity curve by computing vertical projections of the rectangle along the horizontal central line. In one embodiment, the computer program reads pixels of the image portion within the rectangle, and aggregates the pixel values along the direction that is perpendicular to the central line as the intensity curve values along the horizontal central line (X-Axis).

At step 550, the computer program finds a test strip peak on the intensity curve. In the embodiment as illustrated in FIG. 4B, the left peak corresponds to the intensity of a sample line of the test strip. The height of the peak is recorded as the peak value (also referred to as grayscale value) of the sample line of the test strip.

At step 552, the computer program identifies edge pixels by find locations (i.e. pixels) where pixel grayscale value changes radically. At step 555, the computer program performs a Hough transform on edge pixels. to identify a quadrilateral on the upper portion that is defined by two horizontal lines and two vertical lines on the image. In one embodiment, other feature extraction technique, other than the Hough transform, can be used to identify the quadrilateral, as readily understood by a person having ordinary skill in the art.

At step 560, the computer program checks whether a quadrilateral is identified from the upper portion. If a quadrilateral is identified, the computer program continues to step 565. The identified quadrilateral indicates the shape and location of the reference cassette on the image. Otherwise, the computer program stops at step 595.

At step 565, based on the location and dimension of the identified quadrilateral, and a predetermined dimensional relationship between the identified quadrilateral and an inner quadrilateral, the computer program locates the inner quadrilateral within the identified quadrilateral. The inner quadrilateral indicates the shape and location of the reference strip window of the reference cassette on the upper portion of the image.

At step 570, the computer program determines a horizontal central line of the inner quadrilateral. The horizontal central line can be roughly horizontal along the inner quadrilateral. However, the horizontal central line is not required to be at zero degree from any axis of the inner quadrilateral. The horizontal central line is the X-axis of a reference curve to be calculated by the computer program. At step 535, the computer program identifies a rectangle by extending the horizontal central line vertically to a pre-defined distance towards the top and the bottom of the inner quadrilateral. In case when the image of the reference strip window happens to be rectangular, the identified rectangle closely fit the image of the reference strip window.

At step 575, the computer program calculates the reference curve by computing vertical projections of the rectangle along the horizontal central line. In one embodiment, the computer program reads pixels of the image portion within the rectangle, and aggregates the pixel values along the direction that is perpendicular to the central line as the reference curve values along the horizontal central line (X-Axis).

At step 580, the computer program finds four reference strip peaks on the reference curve, corresponding to four reference strips in the reference strip window of the reference cassette. The heights of the peaks are recorded as the peak values (also referred to as grayscale values) of the reference strip.

The steps of analyzing the lower portion (i.e. steps 515-550) and the steps of analyzing the upper portion (i.e. steps 555-580) can be performed by the computer program simultaneously as illustrated in the FIG. 5. In one embodiment, the steps of analyzing the lower portion can be performed before the steps of analyzing the upper portion. In another embodiment, the steps of analyzing the upper portion can be performed before the steps of analyzing the lower portion At step 585, the computer program constructs an interpolation curve (also referred to as standard curve) based on the four peak values of the reference strips and their known intensity values. At step 590, using the peak value (also referred to as grayscale value) value of the test strip, the computer program determines a test strip intensity reading by finding a corresponding interpolation value on the interpolation curve.

Figure 6:
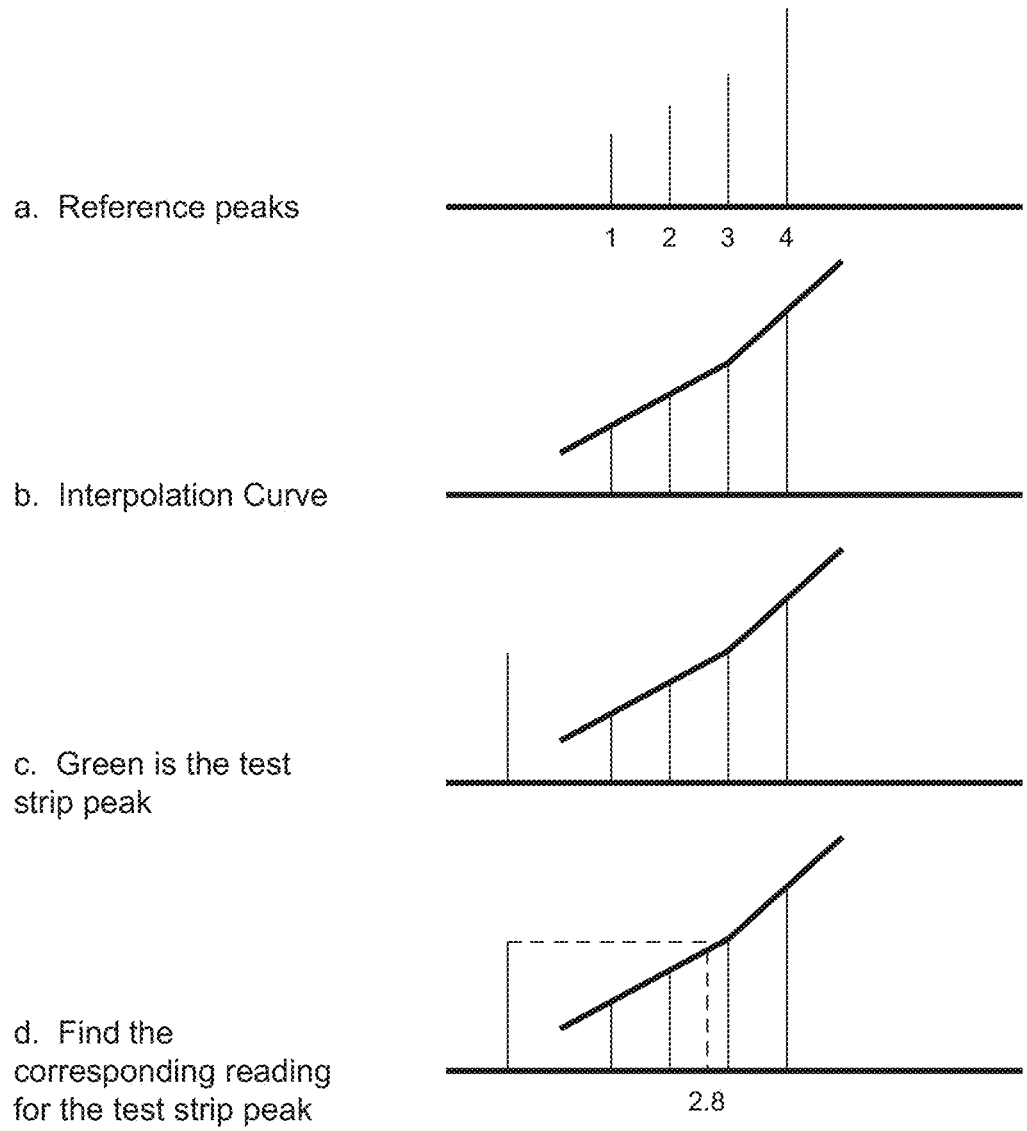
FIG. 6 illustrates an example process of constructing an interpolation curve and finding an interpolation value on the interpolation curve.

There are various ways of constructing the interpolation curve and finding the interpolation value on the interpolation curve, as readily understood by a person having ordinary skill in the art. FIG. 6 illustrates an example process of constructing an interpolation curve (also referred to as standard curve) and finding an interpolation value on the interpolation curve.

At step a, the computer program receives four peak values (also referred to as grayscale values) for the four reference strips generated from the captured image of the reference cassette, as disclosed in step 580 in FIG. 5. The computer program also has four known intensity values for these four reference strips. For each reference strip, the computer program determines a point in an interpolation curve. The X coordinate value of the point is the intensity value of the corresponding reference strip; The Y coordinate value of the point is the peak value (also referred to as grayscale value) of the corresponding reference strip.

At step b, the computer program determines line segments that are bounded by neighboring points. The line segments forms the interpolation curve.

At step c, the computer program receives the peak value (also referred to as grayscale value) for the sample line of the test strip generated from the captured image of the test strip cassette, as disclosed in step 550 in FIG. 5.

At step d, the computer program finds a point on the interpolation curve whose Y coordinate value is the peak value for the test strip. The X coordinate value of the point is the interpolation value, i.e. the test strip intensity reading. Therefore, by comparing the test strip's peak value with the peak values of the reference strips whose intensities are known, the computer program accurately determines the test strip intensity reading, with little interference from the ambient light condition.

The embodiment illustrated in FIG. 6 uses four reference strips (reference lines). In other embodiments, the computer program can use a plurality of reference lines. For example, the computer program can use two reference lines. In that case, the standard curve is assumed to be a linear curve defined by two points located by the know intensities and grayscale values of the two reference lines.

Figure 7:
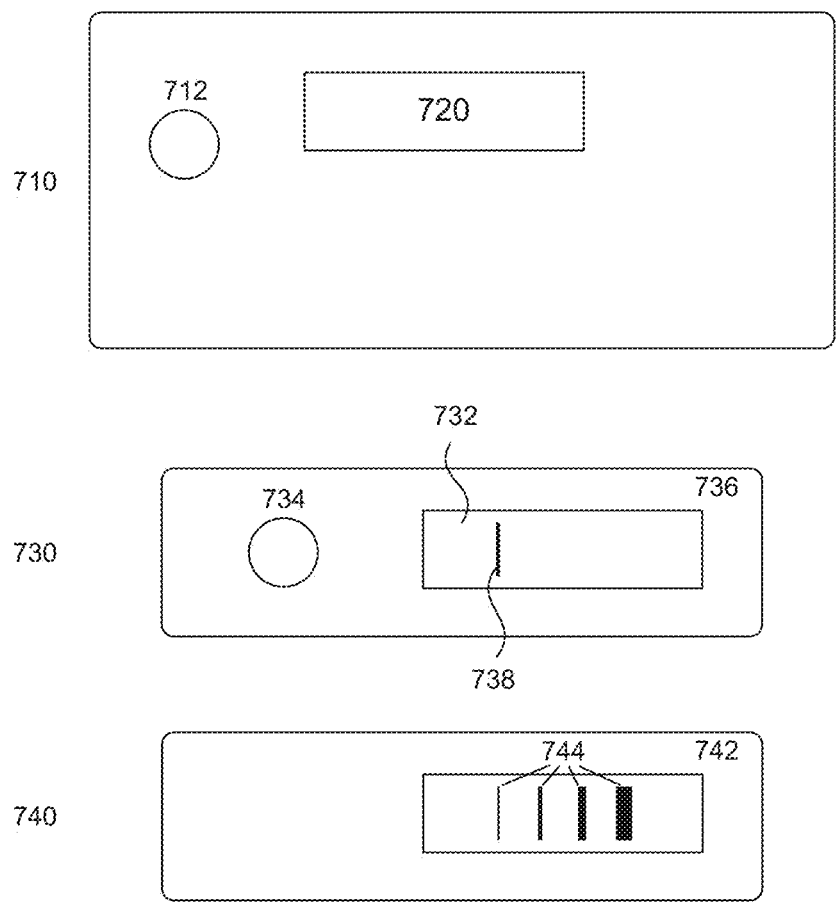
FIG. 7 illustrates an example measurement system based on the test strip intensity recognition techniques.

FIG. 7 illustrates an example measurement system 700 based on the test strip intensity recognition techniques disclosed herein. The measurement system 700 includes a computer device 710. The computer device 710 can be a desktop computer, a laptop, a tablet computer, a smart phone, a personal digital assistant (PDA), a digital camera, or other type of electronic device. The computer device 710 includes a camera 712 capable of capturing images of test strip cassettes. Optionally, the computer device 710 can further include location positioning module, GPRS module, or wireless communication module for transferring the measurement result in real time.

The measurement system 700 further includes a computer program 720 for performing the test strip intensity recognition techniques as disclosed in, for example, FIGS. 3 and 5. The computer program 720 runs on the computer device 710 to control the camera 712 to capture the image and further performs the analysis of the image to recognize the test strip intensity.

The measurement system 700 also includes a test strip cassette 730. The test strip cassette 730 includes a test strip 732 inside of the test strip cassette 730. The test strip cassette 730 can further include a test drop window 734 and a test strip window 736. The test strip cassette 730 can be treated with test fluid, such as urine or blood sample, by dropping the test fluid onto the test drop window 734. Once the test strip cassette 730 is treated with test fluid, one or more strip line 738 will be visualized in the test strip window 736.

In one embodiment, the measurement system 700 can further include a referent strip cassette 740. The reference strip cassette 740 includes a reference strip window 742. Four reference strip lines 744 are visualized in the reference strip window 742. The four reference strip lines 744 have four different known intensities to be compared with the intensity of the test strip line.

In another embodiment, a plurality of reference strip lines is printed on the test strip cassette 730, instead of on a separate reference strip cassette.

Figure 14:
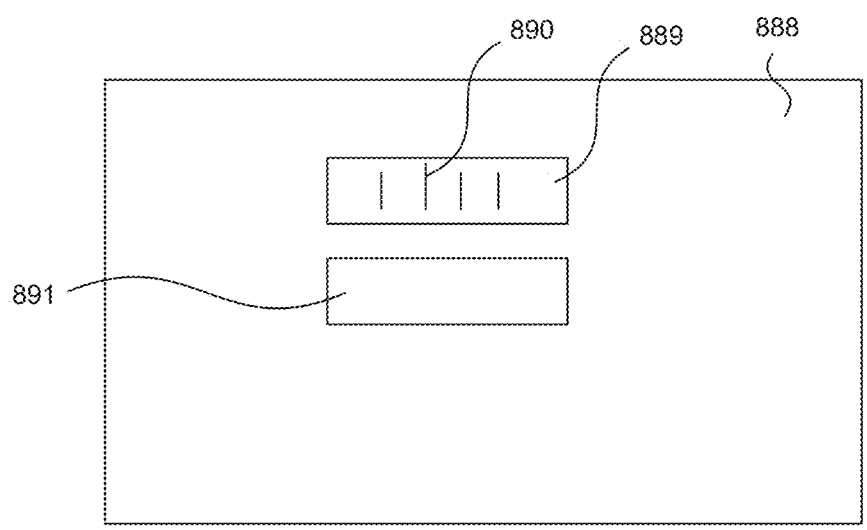
FIG. 14 illustrates a pad with a dark background color having reference strip lines printed on a bright area of the pad.

In yet another embodiment, as illustrated in FIG. 14, a plurality of reference strip lines 890 is printed on a small bright area 889 on a pad 888 (similar to a computer mouse pad) having dark background color. The pad further contains a designed location 891 to put the test cassette. A computer device can capture an image of the pad 888 (including the reference strip lines 890) and the test cassette, in order to process the image and recognize the test strip intensity.

Running on the computer device 710, the computer program 720 can recognize the test strip intensity on the treated test strip cassette 730, calibrated by the reference strip lines 744 on the reference strip cassette 740. The computer program 720 determines a measurement result based on the calibrated test strip intensity.

In one embodiment, the test strip 732 uses colloidal gold immunochromatography technique. The immunochromatography technique is a type of antigen-antibody immune marker technique using colloidal gold as a tracer marker. Colloidal gold is a suspension (or colloid) of particles of gold in a fluid. Gold nanoparticles are produced in a liquid by reduction of chloroauric acid ($H[AuCl_4]$). In the test strip 732, a first specific antigen is attached to a zone of a nitrocellulose membrane. When test fluid reaches one end of the dry nitrocellulose membrane, the antibody and the colloidal gold forms a mixture. Due to the capillary action, the mixture moves along the nitrocellulose membrane. Once the mixture reaches the zone with the first specific antigen, the antibody binds to the antigen. Accordingly the zone shows the color of the colloidal gold. The intensity of the colloidal gold corresponds to the concentration of the antibody.

EXAMPLE

Example 1

Test Strip Intensity Recognition using Single Cassette Mode

Four treated test strip cassettes are prepared for intensity recognition. Each of the test strip cassettes is applied with test fluid containing Immunoglobulin G (IgG) antibody with different concentrations. The concentrations of the IgG test fluid are 0.5 ug/mL, 1 ug/mL, 2 ug/mL, 4 ug/mL, and 8 ug/mL respectively.

A computer device running the above mentioned computer program is used for recognizing the intensities of the test strips on the treated test strip cassettes. For each test strip cassette, the intensity recognition process is repeated 5 times. The background is black. Ambient light condition is typical office light condition. The distance between the computer device and the cassettes during intensity recognition is 9.5 cm. The intensity readings are listed in the Table 1.

TABLE 1

| Concentration (ug/mL IgG) | Log of concentration | Repeat 1 | Repeat 2 | Repeat 3 | Repeat 4 | Repeat 5 | mean intensity | stdev | cv |
|---|---|---|---|---|---|---|---|---|---|
| 0.5 | −0.693147181 | 0.1 | 0.09 | 0.09 | 0.08 | 0.08 | 0.088 | 0.008367 | 9.5075 |
| 1 | 0 | 0.1 | 0.12 | 0.12 | 0.13 | 0.12 | 0.118 | 0.010954 | 9.283433 |
| 2 | 0.693147181 | 0.18 | 0.22 | 0.18 | 0.18 | 0.18 | 0.188 | 0.017889 | 9.515183 |
| 4 | 1.386294361 | 0.22 | 0.22 | 0.27 | 0.23 | 0.25 | 0.238 | 0.021679 | 9.109027 |
| 8 | 2.079441542 | 0.35 | 0.36 | 0.35 | 0.35 | 0.35 | 0.352 | 0.004472 | 1.270493 |

Figure 8A:
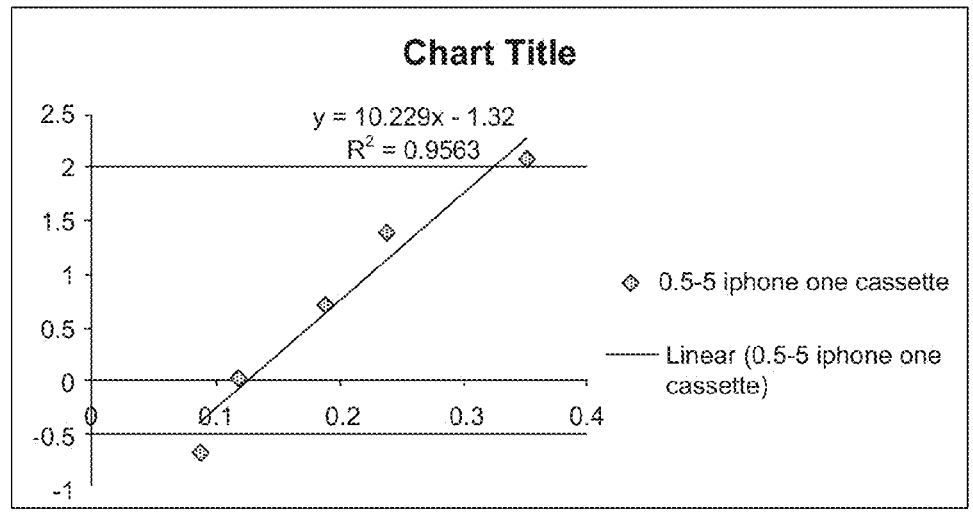
FIG. 8A shows a linear regression analysis on the experimental data for single cassette mode test strip intensity recognition.

FIG. 8A shows a linear regression analysis on the experimental data for single cassette mode test strip intensity recognition. The horizontal coordinates of the data points on FIG. 8A are the average number of the intensity readings repeated 5 times for each test strip cassettes. The vertical coordinates of the data points are the concentrations of the IgG antibody applied to the test strip fluid.

Figure 8B:
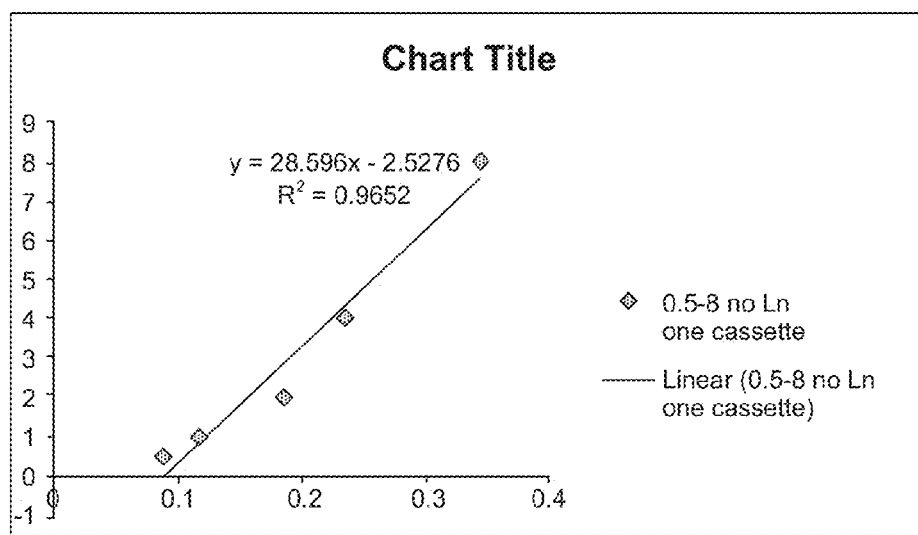
FIG. 8B shows a linear regression analysis on the experimental data for single cassette mode test strip intensity recognition in view of the logarithms of the IgG concentrations.

FIG. 8B shows a linear regression analysis on the experimental data for single cassette mode test strip intensity recognition in view of the logarithms of the IgG concentrations. The horizontal coordinates of the data points on FIG. 8B are the average number of the intensity readings repeated 5 times for each test strip cassettes. The vertical coordinates of the data points are the logarithms of concentrations of the IgG antibody applied to the test strip fluid.

Example 2

Test Strip Intensity Recognition Using Double Cassette Mode

Four treated test strip cassettes are prepared for intensity recognition. Each of the test strip cassettes is applied with test fluid containing Immunoglobulin G (IgG) antibody with different concentrations. The concentrations of the IgG test fluid are 0.5 ug/mL, 1 ug/mL, 2 ug/mL, 4 ug/mL, and 8 ug/mL respectively. A reference cassette showing four reference strips with different known intensities are used as reference for intensity recognition.

A computer device running the above mentioned computer program is used for capture the images of the test strip cassettes along with the reference cassette. The computer program performs the recognition of the intensities of the test strips on the treated test strip cassettes based on the images. For each test strip cassette, the intensity recognition process is repeated 5 times. The background is black. Ambient light condition is typical office light condition. The distance between the computer device and the cassettes during intensity recognition is 9.5 cm. The distance between each test strip cassette and the reference cassette is 1.0 cm. The intensity readings are listed in the Table 2.

TABLE 2

| Concentration (ug/mL IgG) | Log of concentration | Repeat 1 | Repeat 2 | Repeat 3 | Repeat 4 | Repeat 5 | mean intensity | stdev | cv |
|---|---|---|---|---|---|---|---|---|---|
| 0.5 | −0.693147181 | 2.68 | 2.64 | 2.66 | 2.66 | 2.66 | 2.66 | 0.014142 | 0.531659 |
| 1 | 0 | 2.66 | 2.8 | 2.64 | 2.68 | 2.78 | 2.712 | 0.072938 | 2.689466 |
| 2 | 0.693147181 | 2.94 | 3.02 | 2.96 | 2.96 | 2.96 | 2.968 | 0.030332 | 1.021951 |
| 4 | 1.386294361 | 3.18 | 3.24 | 3.16 | 3.16 | 3.14 | 3.176 | 0.038471 | 1.211296 |
| 8 | 2.079441542 | 3.42 | 3.46 | 3.52 | 3.52 | 3.54 | 3.492 | 0.0502 | 1.43756 |

Figure 9A:
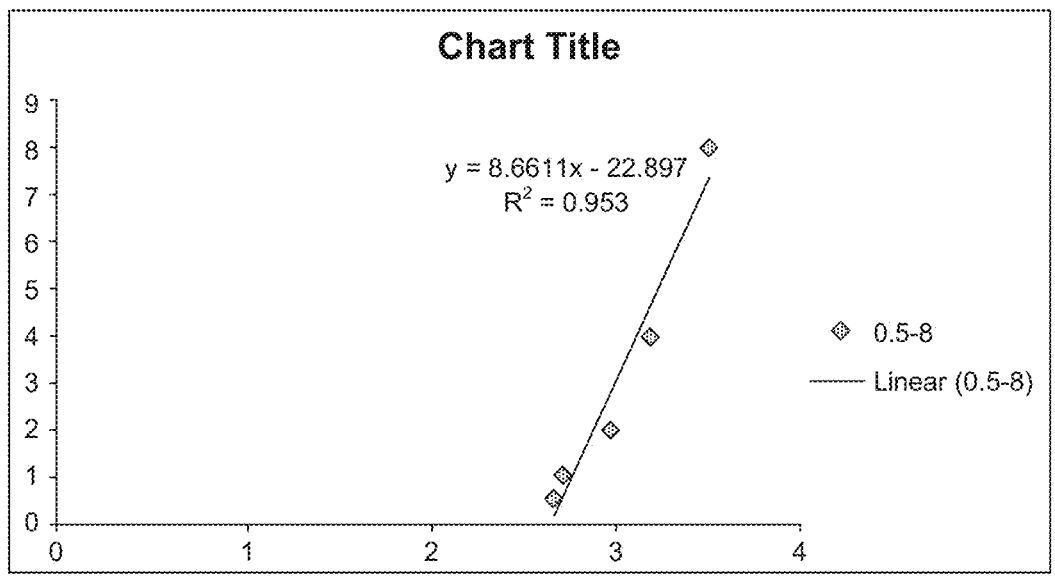
FIG. 9A shows a linear regression analysis on the experimental data for double cassette mode test strip intensity recognition.

FIG. 9A shows a linear regression analysis on the experimental data for double cassette mode test strip intensity recognition. The horizontal coordinates of the data points on FIG. 9A are the average number of the intensity readings repeated 5 times for each test strip cassette. The vertical coordinates of the data points are the concentrations of the IgG antibody applied to the test strip fluid.

Figure 9B:
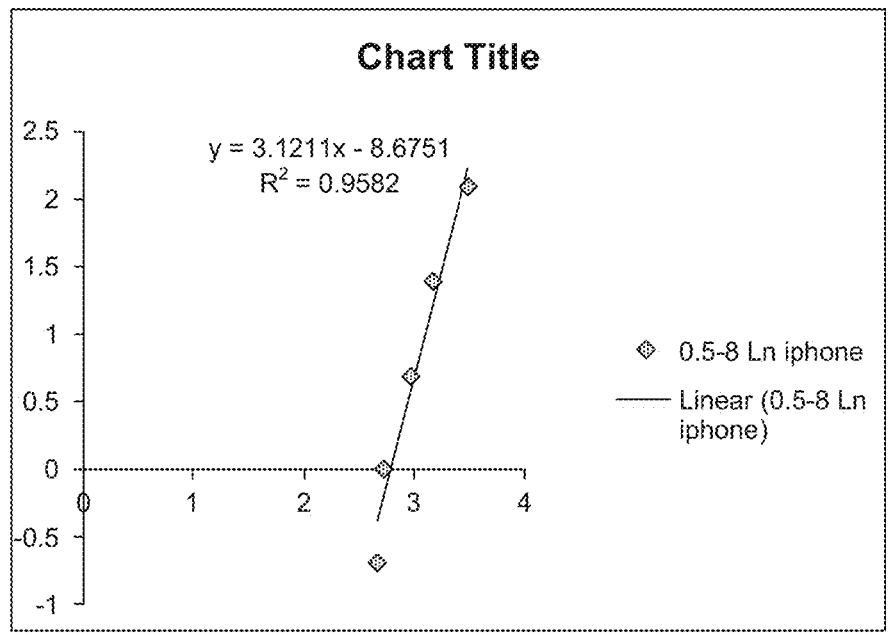
FIG. 9B shows a linear regression analysis on the experimental data for double cassette mode test strip intensity recognition in view of the logarithms of the IgG concentrations.

FIG. 9B shows a linear regression analysis on the experimental data for double cassette mode test strip intensity recognition in view of the logarithms of the IgG concentrations. The horizontal coordinates of the data points on FIG. 9B are the average number of the intensity readings repeated 5 times for each test strip cassette. The vertical coordinates of the data points are the logarithms of concentrations of the IgG antibody applied to the test strip fluid. FIG. 9B shows that the logarithms of the IgG concentrations have a strong linear relationship with the intensity readings of the test strip. The linear coefficient is 0.9582. The coefficient of variation is less than 3% for each test strip cassette sample.

Although the examples show using the technique to accurately recognize intensities of the test strips. The technique can be also used to accurately recognize colors of the test strips, as readily understood by a person having ordinary skill in the art.

Figure 10:
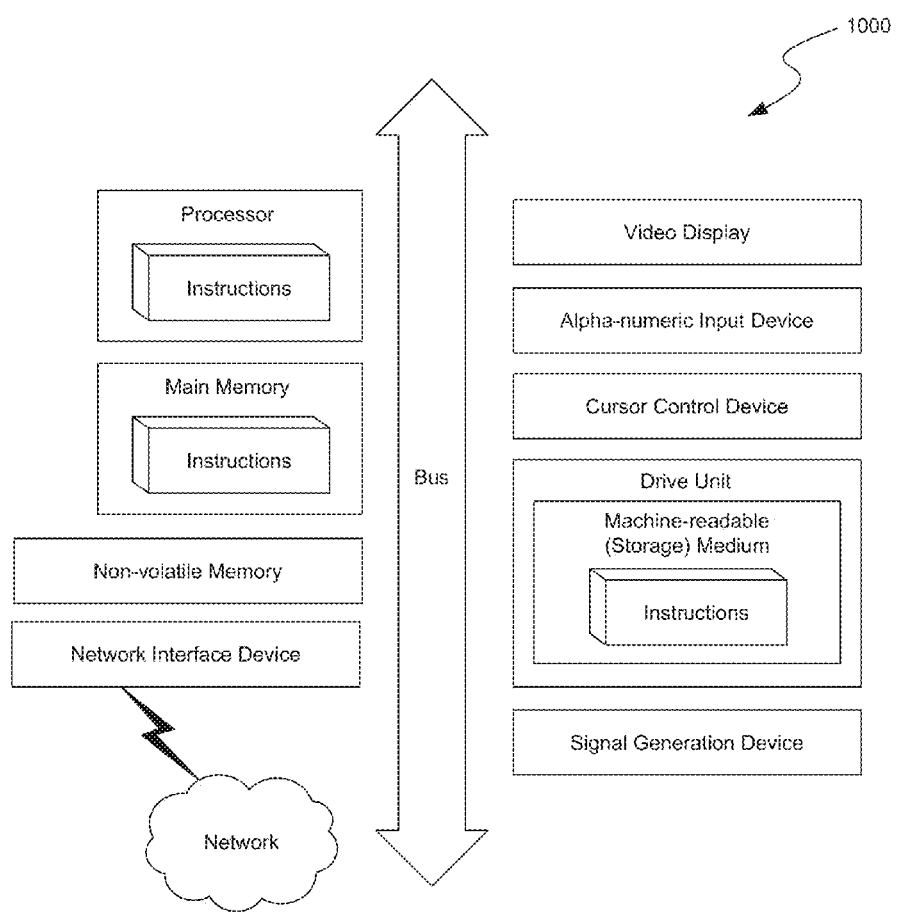
FIG. 10 shows a diagrammatic representation of a machine in the example form of a computer device within which a set of instructions, for causing the machine to perform any one or more of the methodologies discussed herein, may be executed.
Figure 11:
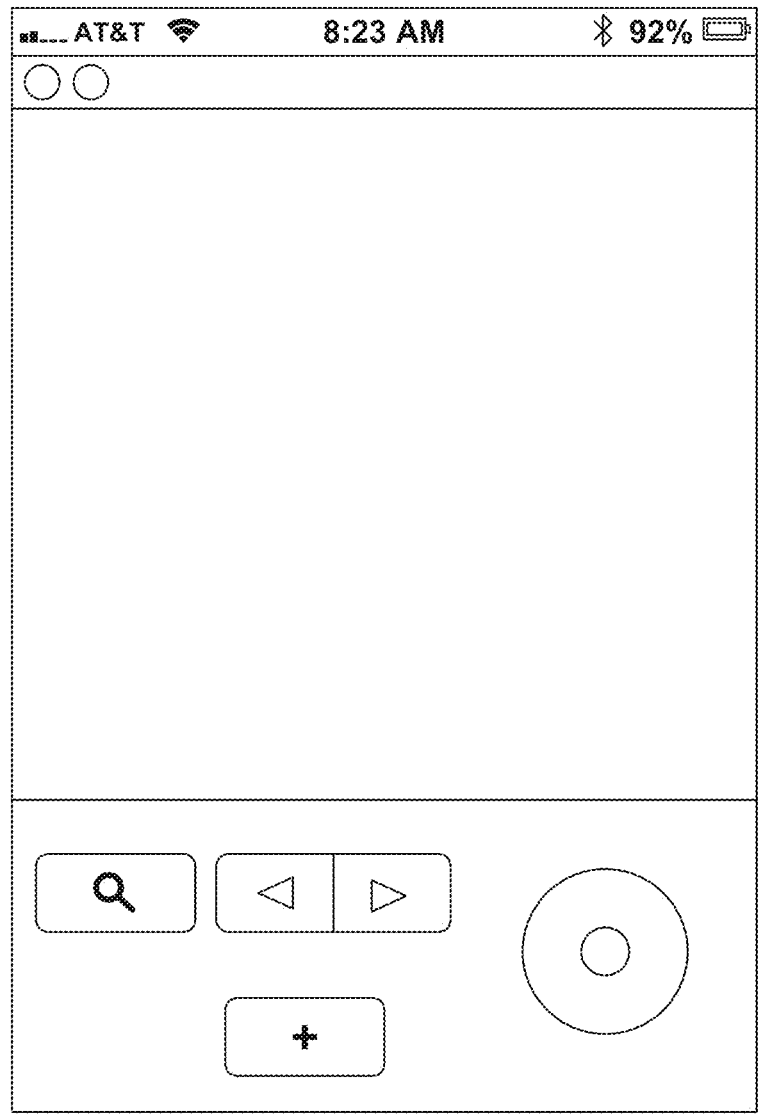
FIG. 11 illustrates a screenshot showing an interface of an example computer program for capturing cassette images and recognizing test strip intensities.
Figure 12:
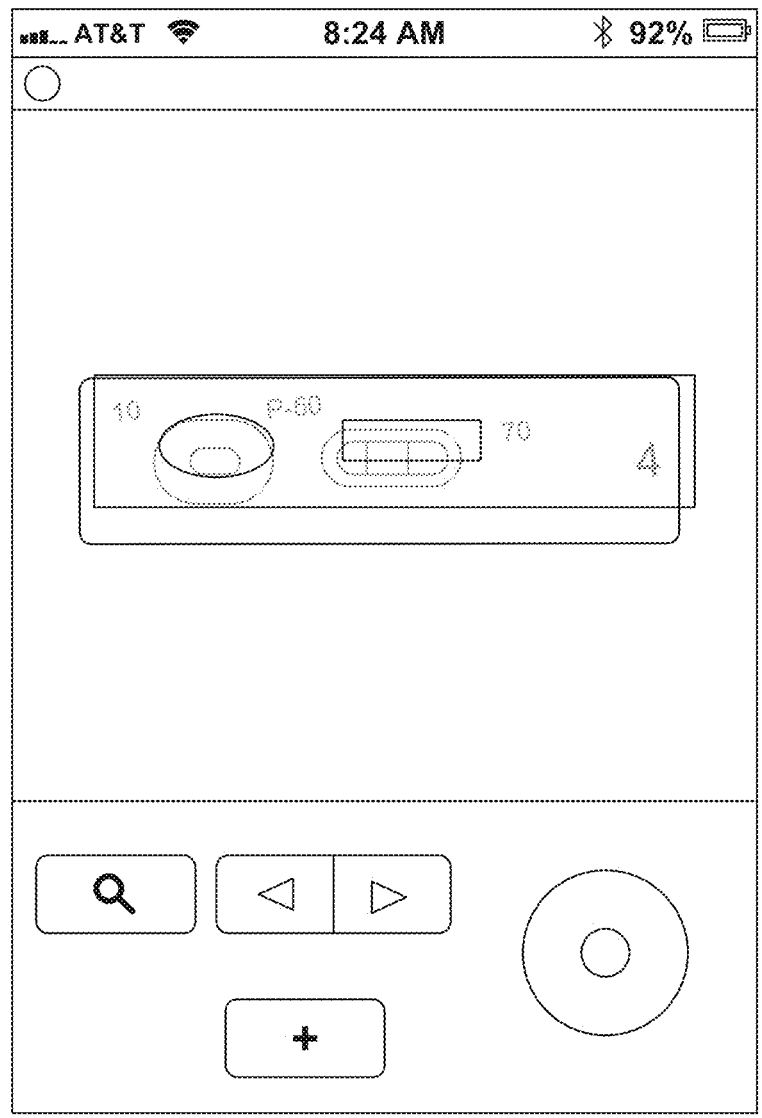
FIG. 12 illustrates a screenshot showing a single cassette mode capture interface of the example computer program.
Figure 13:
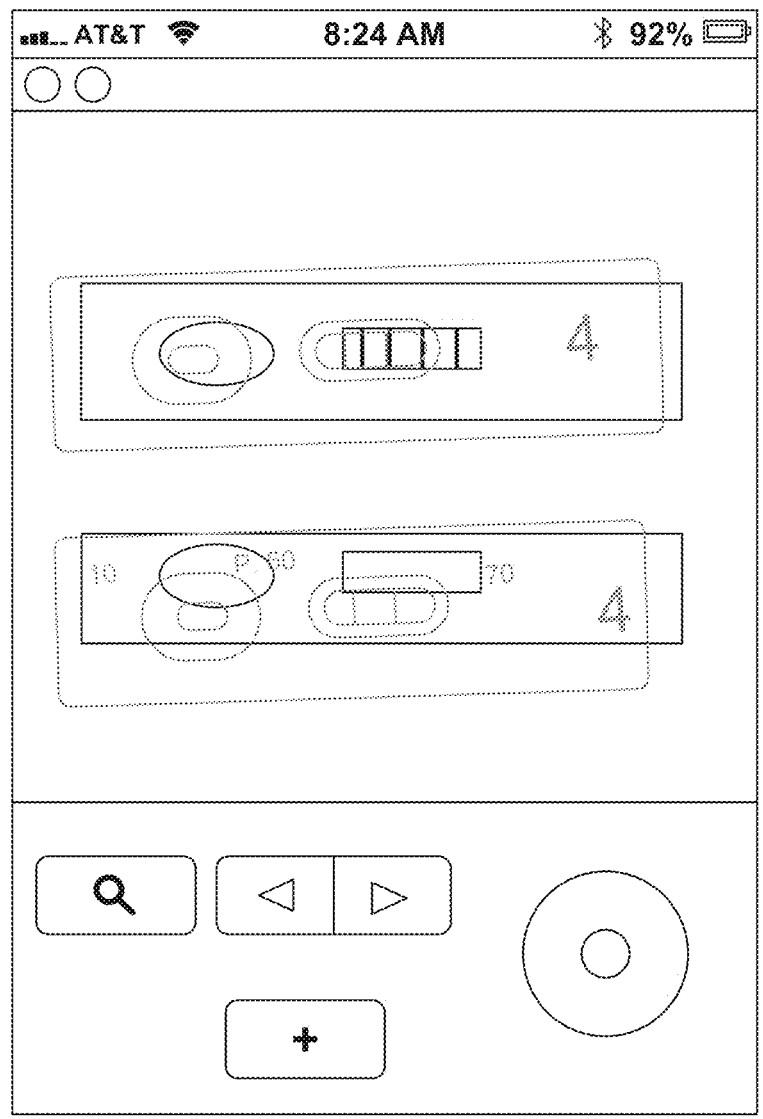
FIG. 13 illustrates a screenshot showing a double cassette mode capture interface of the example computer program.

FIG. 10 shows a diagrammatic representation of a machine in the example form of a computer device within which a set of instructions, for causing the machine to perform any one or more of the methodologies discussed herein, may be executed.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a user device, a tablet PC, a laptop computer, a set-top box (STB), a personal digital assistant (PDA), a cellular telephone, an iPhone, an iPad, a Blackberry, a processor, a telephone, a web appliance, a network router, switch or bridge, a console, a hand-held console, a (handheld) gaming device, a music player, any portable, mobile, hand-held device, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer devices, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

The network interface device enables the machine to mediate data in a network with an entity that is external to the host server, through any known and/or convenient communications protocol supported by the host and the external entity. The network interface device can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network interface device can include a firewall which can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

Other network security functions can be performed or included in the functions of the firewall, can be, for example, but are not limited to, intrusion-prevention, intrusion detection, next-generation firewall, personal firewall, etc. without deviating from the novel art of this disclosure.

The invention claimed is:

1. A method for determining the intensity of a test strip comprising:
    obtaining, by a processor, an image comprising a sample line in a test strip and a plurality of reference lines in a test strip from a test cassette, wherein the reference lines have known intensities;
    identifying, by the processor, from the image a first quadrilateral having the sample line and a second quadrilateral having the reference lines;
    determining, by the processor, a grayscale value of the sample line from the first quadrilateral and grayscale values of the reference lines from the second quadrilateral by vertical projections of pixel values by:
        determining a first horizontal central line of the second quadrilateral,
        conducting vertical projections of pixel values of the second quadrilateral along the first horizontal central line, and
        selecting peak values as the grayscale values of the reference lines among the vertical projections of the pixel values of the second quadrilateral;
    constructing, by the processor, a standard curve based on the grayscale values of the reference lines versus the known intensities of the reference lines; and
    determining, by the processor, the intensity of the sample line by fitting the grayscale value of the sample line on the standard curve.

2. The method of claim 1, wherein the determining grayscale value of the sample line from the first quadrilateral and grayscale values of the reference lines from the second quadrilateral by vertical projections of pixel values comprises:
    determining a second horizontal central line of the first quadrilateral;
    conducting vertical projections of pixel values of the first quadrilateral along the second horizontal central line; and
    selecting a peak value as the grayscale value of the sample line among the vertical projections of the pixel values of the first quadrilateral.

3. The method of claim 1, further comprising:
    determining a test fluid concentration based on the intensity of the sample line.

4. The method of claim 1, further comprising:
    adjusting a position and an angle of a camera device for capturing the image by visualizing an overlay frame.

5. The method of claim 1, further comprising:
    adjusting a position and an angle of a test cassette containing the test strip for capturing the image by visualizing an overlay frame.

6. The method of claim 1, further comprising:
    adjusting a position and an angle of a reference cassette containing the reference lines for capturing the image by visualizing an overlay frame.

7. The method of claim 1, wherein the test strip is installed inside of the cassette.

8. The method of claim 1, wherein the reference lines are printed on a reference strip cassette.

9. The method of claim 1, wherein the reference lines are printed on the test cassette.

10. The method of claim 1, wherein the reference lines are printed on a bright area of a pad having a dark background color.

11. The method of claim 1, wherein the identifying from the image the first quadrilateral having the sample line and the second quadrilateral having the reference lines comprises:
    determining a division line for the image, the division line dividing the image into a top portion and a bottom portion;
    identifying edge pixels at locations where pixel grayscale value changes radically;
    performing a feature extraction process on the edge pixels in the first portion to identify the first quadrilateral; and
    performing a feature extraction process on the edge pixels in the second portion to identify the second quadrilateral.

12. The method of claim 1, further comprising:
    locating an first inner quadrilateral within the first quadrilateral, based on location and dimension of the first quadrilateral and a predetermined dimensional relationship between the first inner quadrilateral and the first quadrilateral;
    determining a horizontal central line of the first inner quadrilateral;
    conducting vertical projections of pixel values of the first inner quadrilateral along the horizontal central line; and
    selecting a peak value as the grayscale value of the sample line among the vertical projections of the pixel values of the first inner quadrilateral.

13. The method of claim 1, further comprising:
    locating an second inner quadrilateral within the second quadrilateral, based on location and dimension of the second quadrilateral and a predetermined dimensional relationship between the second inner quadrilateral and the second quadrilateral;
    determining a horizontal central line of the second first quadrilateral;
    conducting vertical projections of pixel values of the second inner quadrilateral along the horizontal central line; and
    selecting peak values as the grayscale values of the reference lines among the vertical projections of the pixel values of the second inner quadrilateral.

14. The method of claim 1, wherein a reference cassette separated from the test cassette is introduced to compensate a measurement difference from changes of ambient light condition.

15. The method of claim 14, wherein a plurality of reference lines having known intensities are installed inside of the reference cassette.

* * * * *